(12) United States Patent
Mihara et al.

(10) Patent No.: US 6,731,716 B2
(45) Date of Patent: May 4, 2004

(54) X-RAY CT APPARATUS

(75) Inventors: Kazumasa Mihara, Hiroshima-ken (JP); Keiichi Hori, Hyogo-ken (JP); Yuichiro Kaminou, Aichi-ken (JP); Setuta Setogawa, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 10/277,051

(22) Filed: Oct. 22, 2002

(65) Prior Publication Data

US 2003/0043958 A1 Mar. 6, 2003

Related U.S. Application Data

(63) Continuation of application No. PCT/JP02/01621, filed on Feb. 22, 2002.

(30) Foreign Application Priority Data

Feb. 23, 2001 (JP) ........................................ 2001-049258

(51) Int. Cl.$^7$ ................................................. A61B 6/03
(52) U.S. Cl. ................................ 378/9; 378/4; 378/147
(58) Field of Search ................................ 378/147, 149, 378/9, 10, 4, 145

(56) References Cited

U.S. PATENT DOCUMENTS

| 5,034,970 | A | * | 7/1991 | Yahata et al. | ................. | 378/20 |
| 5,550,886 | A | * | 8/1996 | Dobbs et al. | ................. | 378/19 |
| 6,366,642 | B1 | * | 4/2002 | Andrews | ..................... | 378/130 |
| 2003/0072407 | A1 | * | 4/2003 | Mihara et al. | ................. | 378/4 |
| 2003/0076921 | A1 | * | 4/2003 | Mihara et al. | ................. | 378/4 |

FOREIGN PATENT DOCUMENTS

| JP | 55-46408 | | 4/1980 | | |
| JP | 58-115738 | | 7/1983 | | |
| JP | 9-248300 | | 9/1997 | | |
| JP | 10-75944 | | 3/1998 | | |
| JP | 10-295682 | * | 11/1998 | ............ | A61B/6/03 |

* cited by examiner

Primary Examiner—David V. Bruce
Assistant Examiner—Chih-Cheng Glen Kao
(74) Attorney, Agent, or Firm—Armstrong, Kratz, Quintos, Hanson & Brooks, LLP

(57) ABSTRACT

An X-ray CT apparatus comprises a large number of X-ray sources, a detector, and a collimator. The X-ray sources are arranged around an object P of inspection. The detector detects X rays emitted from the X-ray sources. The collimator is located between the X-ray sources and the object of inspection, and restricts the angle of emission of the X rays emitted from the X-ray sources so as to match the size of the detection surface of the detector.

10 Claims, 5 Drawing Sheets

X-RAY CT APPARATUS

CROSS-REFERENCE TO RELATED APPLICATIONS

This is a Continuation Application of PCT Application No. PCT/JP02/01621, filed Feb. 22, 2002, which was not published under PCT Article 21(2) in English.

This application is based upon and claims the benefit of priority from the prior Japanese Patent Application No. 2001-049258, filed Feb. 23, 2001, the entire contents of which are incorporated herein by reference.

BACKGROUND OF THE INVENTION

1. Field of the Invention

The present invention relates to an X-ray CT apparatus capable of obtaining a tomographic image of an object of inspection in a short time.

2. Description of the Related Art

An X-ray CT (Computed Tomography) apparatus comprises an X-ray tube and a detector that are located on either side of an object of inspection. The X-ray tube emits the X rays toward the object of inspection, and the detector detects the X rays emitted from the X-ray tube. Based on the difference in the rate of X-ray absorption between parts in the object of inspection, the X-ray CT apparatus analyzes, by using a computer, transmitted X-ray data that the detector detects each time when X rays are applied to the object of inspection in many directions, and obtains a tomographic image of the object of inspection.

There is an X-ray CT apparatus of an R—R (rotate—rotate) type in which the X-ray tube and detector rotate around the object of inspection while maintaining their relative positions. In the case where the X-ray CT apparatus of this type is used for diagnosis in the medical field, however, it involves mechanical movement such that the X-ray tube and the detector rotate around a patient, the object of inspection, so that the taking time (scanning time), which is necessary to obtain one tomographic image, is long.

There is also an X-ray CT apparatus of another type. This X-ray CT apparatus comprises an electron gun, a magnetic field coil, and a target ring instead of the X-ray tube. The electron gun is located on the central axis of the target ring. An electron beam shot from the electron gun toward the center of the target ring is bent by the magnetic field coil, whereupon it hits the target ring. When the target ring is hit by the electron beam, it emits an X-ray toward an object of inspection located inside the target ring. The X-ray CT apparatus changes the position for the impact of the electron beam in the circumferential direction of the target ring by changing the direction of the magnetic field that the magnetic field coil generates. By doing this, the X-ray CT apparatus applies X rays to the object of inspection in many directions, and obtains a tomographic image in accordance with the resulting transmitted X-ray data. In the X-ray CT apparatus of this type, the X-ray source is moved electrically, so that the taking time can be made shorter than in the case of the X-ray CT apparatus of the R—R type. However, there is a limit to shorten the time for acquiring a tomographic image, because the X-ray source is only one in number at the same time and a detector takes time to detect the necessary dose of X rays.

In the industrial field, there is proposed an X-ray CT apparatus for observing the movement of air bubbles in two-phase flow, for example. As an example of this X-ray CT apparatus, there is an X-ray CT apparatus comprising a large number of X-ray sources as described in Jpn. Pat. Appln. KOKAI Publication No. 9-248300, 10-75944, or 10-295682.

The X-ray CT apparatuses described in Jpn. Pat. Appln. KOKAI Publications Nos. 9-248300 and 10-75944 use a large number of X-ray tubes as X-ray sources. In the case described in Jpn. Pat. Appln. KOKAI Publication No. 10-75944, X rays are simultaneously applied from two or more X-ray tubes on condition that regions on the detector upon which X rays are incident never overlap one another.

The X-ray CT apparatus described in Jpn. Pat. Appln. KOKAI Publication No. 10-295682 comprises a vacuum chamber, a large number of X-ray sources, and a detector. The vacuum chamber is in the shape of a ring that surrounds the object of inspection. The numerous X-ray sources are arranged in a circumferential direction in the vacuum chamber, and emit X rays in fan beam that crosses the object of inspection toward the object of inspection. The detector is in the shape of a ring that surrounds the object of inspection in a position on the inner peripheral side of the vacuum chamber, and serves to detect the X rays that are emitted from the X-ray sources and passed through the object of inspection. The X-ray sources are actuated one after another in the order of arrangement and emit the fan-shaped X rays toward the object of inspection. The emitted X rays are passed through the object of inspection and detected by the detector on the opposite side. A tomographic image can be obtained in a short time by quickly switching signals that serve to actuate the X-ray sources.

Accordingly, application of industrial X-ray CT apparatuses to an examination in the medical field is under investigation. When a patient is performed diagnosis by using an industrial X-ray CT apparatus, the taking time for the acquisition of a tomographic image can be shortened considerably, so that improvement of the efficiency of diagnosis can be expected. Since the industrial X-ray CT apparatus can acquire a tomographic image in a short time, moreover, an image can be obtained corresponding to change that is occurred in a short time.

In the case where X rays are generated by utilizing an electron beam, X rays are emitted in all directions from the spot that is hit by the electron beam. However, no consideration is given to the spread angle of the fan-beams that are emitted from the X-ray sources of the industrial X-ray CT apparatus. Thus, the object of inspection is irradiated with unnecessary X rays that are not detected by means of the detector.

Further, no consideration is given to the spread angle of X rays in the industrial X-ray CT apparatus. When the X-ray CT apparatus irradiates the fan-beams from three or more X-ray sources to the object of inspection at a time, the X rays inevitably interfere with one another in some regions on the detector and a high-precision tomographic image cannot be obtained. Therefore, the X rays must be emitted from opposite positions at 180° from each other in order to apply the X rays without interference. In the case where the X-ray CT apparatus irradiates the fan-beams from two X-ray sources to the object of inspection at a time, the two X-ray sources must be switched so that they always maintain their symmetrical positions with respect to the object of inspection. The time for taking the acquisition of one tomographic image is restricted by the time that is necessary to switch each X-ray source around the object of inspection by a half turn.

The X-ray CT apparatus for diagnosis in the medical field must apply the X rays to the object of inspection in as many directions as possible to acquire transmitted X-ray data in order to obtain a fine tomographic image. In the case where the industrial X-ray CT apparatus is applied to the medical field, therefore, the X-ray sources must be increased in number.

When the directions in which X rays are applied is increased, however, the dose of X rays applied to the patient inevitably increases, and the taking time is prolonged, so that the load on the patient increases.

The purpose of the present invention is to provide an X-ray CT apparatus designed so that the dose of X rays applied to the object of inspection can be reduced, and that the time, which is necessary to acquire a tomographic image of the object of inspection, can be shortened.

BRIEF SUMMARY OF THE INVENTION

An X-ray CT apparatus according to one embodiment of the present invention is designed to reduce the dose of X rays applied to an object of inspection and to shorten the time that is necessary to acquire a tomographic image of the object of inspection.

An X-ray CT apparatus according to one embodiment of the present invention includes a large number of X-ray sources, a detector, and a collimator. The X-ray sources are arranged around the object of inspection. The detector detects X rays emitted from the X-ray sources. The collimators are located between the X-ray sources and the object of inspection, thereby restricting those X rays that, among the X rays emitted from the X-ray sources, are not applied to the detection surface of the detector.

An X-ray CT apparatus according to another embodiment of the present invention includes a main body, a large number of X-ray sources, a vacuum chamber, a collimator, a detector, a bed, and a beam limiter. The main body has a hole in which an object of inspection is located. The X-ray sources are concentrically arranged around the hole. The vacuum chamber is in the form of a ring surrounding the hole and holds the X-ray sources. The collimator is mounted along the inner peripheral wall of the vacuum chamber and has through holes corresponding to the individual X-ray sources. The detector includes a large number of detection elements for detecting the X rays emitted from the X-ray sources. The detection elements are arranged densely in the shape of a cylinder having the same central axis with a concentric circle composed of the X-ray sources, with the detection surface thereof facing toward the central axis. The bed has a slide mechanism and a lift device and serves to position the object of inspection in the hole of the main body. The beam limiter is located between the X-ray sources and the object of inspection and serves to restrict the spread of the X rays in the direction along the central axis of the concentric circle composed of the X-ray sources within the width of the detector in the direction along the central axis.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
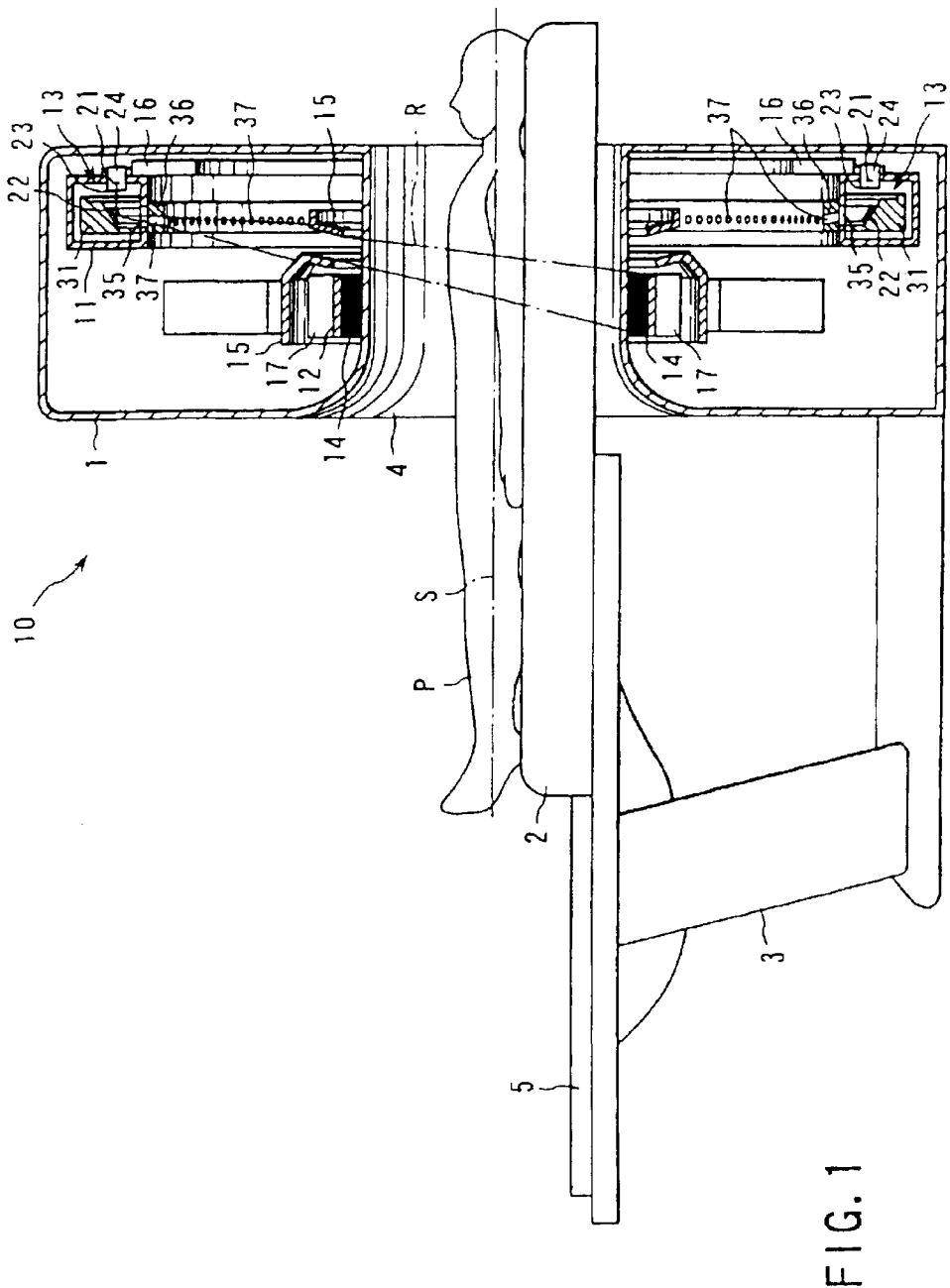
FIG. 1 is a sectional side view typically showing an X-ray CT apparatus according to one embodiment of the present invention.

An X-ray CT apparatus 10 for diagnosis that is utilized in the medical field will be described as an example according to one embodiment of the present invention with reference to FIGS. 1 to 8. The X-ray CT apparatus 10 shown in FIG. 1 uses X-ray sources 13 that emit X rays R by applying electron beams e from an electron gun to a target. The X-ray CT apparatus 10 shown in FIG. 1 comprises a main body 1 and a bed 2 that carries thereon a patient P as an object of detection. The main body 1 is in the form of a doughnut that has a horizontal central axis S. A hole 4 that opens in the central portion of the main body 1 is of a size such that it allows the patient P on the bed 2 to be horizontally inserted therein. The bed 2 is provided with a lift device 3 and a slide mechanism 5. The lift device 3 can make the body axis of the patient P incline at an angle to or extend parallel to the central axis S of the main body 1. The slide mechanism 5 moves the patient P along the body axis. Thus, the bed 2 can allow the patient P to be inserted into the hole 4 and hold the patient P in any desired position. Since the bed 2 is expected only to be able to hold the patient P relative to the hole 4 of the main body 1, the main body 1 may be moved with respect to the bed 2 or both may be moved individually.

Figure 2:
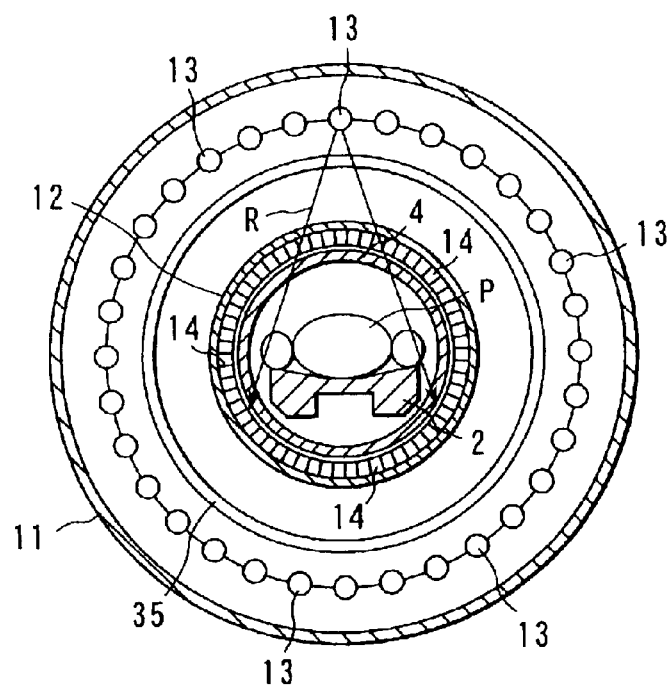
FIG. 2 is a sectional view as taken from the front of the X-ray CT apparatus, typically showing a vacuum chamber, X-ray sources, and a detector of FIG. 1.

As shown in FIG. 2, the main body 1 is provided with a large number of X-ray sources 13 concentrically arranged around the hole 4 and a detector 12 for detecting the X rays R emitted from the X-ray sources 13. The X-ray sources 13 are held in a vessel (vacuum chamber) 11 inside which a vacuum is maintained. The vacuum chamber 11 is in the form of a ring that has its center on the central axis S.

Figure 4:
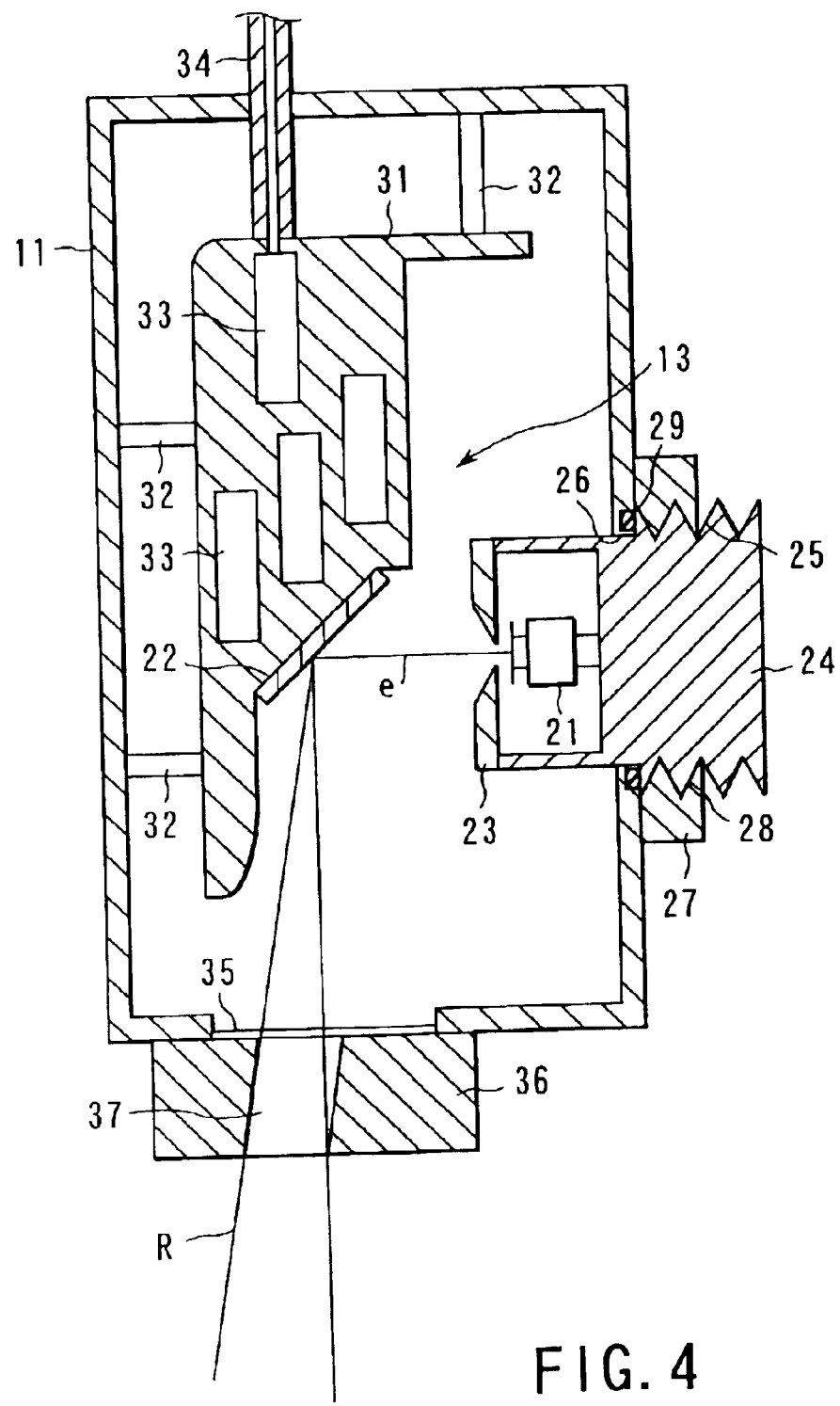
FIG. 4 is a view typically showing a profile of the vacuum chamber of FIG. 1.

As shown in FIG. 4, the profile of the vacuum chamber 11 is square. The detector 12 is in the form of a ring that is located inside the vacuum chamber 11 and has its center on the central axis S. The vacuum chamber 11 and the detector 12 are offset with respect to each other along the central axis S. The X-ray sources 13 are arranged at equal distance along the vacuum chamber 11.

Each X-ray sources 13, like a triode, comprises a cathode 21, an anode 22, and a gate 23. A high voltage is applied between the cathode 21 and the anode 22. The cathode 21 has a filament that emits thermions when heated. The filament is a coiled one, for example, and generates heat attributable to resistance heating when energized. As a potential that is opposite to the thermions in polarity is applied to anode 22, the thermions are attracted to the target on a part of the anode and accelerated. The accelerated thermions form electron beams, which run against the target. The target, which is formed of, e.g., tungsten, emits X rays from that area which is hit by the thermions. Since the target is heated with collision energy of the thermions, the anode 22 is made of a material such as copper that has high heat conductivity. The gate 23 prevents the thermions from being emitted toward the anode 22 as it is located between the cathode 21 and the anode 22 and is supplied with potential of the same polarity with the thermions. The cathode 21 and gate 23 function as the electron gun. The cathode 21 and the gate 23 are mounted on a holding member 24. A screw 25 is formed on the outer peripheral surface of the holding member 24.

The sidewall of the vacuum chamber 11 is provided with a hole 26 to which the holding member 24 is attached. A mounting member 27 for positioning the holding member 24 is attached to the edge portion of the hole 26. A screw 28 is formed on the inner peripheral surface the mounting member 27. Further, a sealing member 29 is fitted in a recess that is formed in the edge of the hole 26 which is in contact with the holding member 24 so as to surround the hole 26. The sealing member 29 may be fitted in a recess that is formed in the holding member 24 so that the vacuum chamber 11 can be kept airtight.

The holding member 24 is fixed to the vacuum chamber 11 in a manner such that the screw 25 of the holding member 24 and the screw 28 of the mounting member 27 mesh with each other. The holding member 24 is attached to the sidewall of the vacuum chamber 11 so that the direction of emission of the electron beams is parallel to the central axis S. The cathode 21 and the gate 23 project inside the vacuum chamber 11. The mounting member 27 is provided so that the position of irradiation of the target with the electron beams that are emitted from the cathode 21 can be shifted.

A support member 31 is attached to the inner surface of the vacuum chamber 11 by an insulating member 32. The support member 31 is in the form of a ring that extends along the inner periphery of the vacuum chamber 11 and has its center on the central axis S. The anode 22 is attached to the support member 31 so as to receive the electron beams that are emitted from the cathode 21. The surface of the anode 22 which receives the electron beams slightly tilts toward the central axis S so that the X rays R can be emitted toward the detector 12.

The support member 31 is formed of a material with high heat conductivity and is provided internally with a cooling water channel 33 throughout the circumference. A cooling water pipe 34 is connected to the cooling water channel 33. Cooling water is fed through the cooling water pipe 34 and circulated in the cooling water channel 33 by a cooling device (not shown). Thus, the anode 22 that is heated with the energy of the electron beams can be cooled indirectly. Although only one cooling water pipe 34 is shown in FIG. 4, at least two are provided for water supply and drainage in order to circulate the cooling water.

A window 35 through which the X rays R generated from the X-ray sources 13 are transmitted toward the detector 12 is provided in the inner peripheral wall of the vacuum chamber 11 so as to extend continuously throughout the circumference. Outside the inner peripheral wall of the vacuum chamber 11, a collimator 36 is mounted along the window 35. The collimator 36 has a width greater than that of the window 35 in the direction along the central axis S. The collimator 36 is made of a metallic material such as tungsten or zinc that absorbs the X rays R at a high rate. The collimator 36 is provided with through holes 37, which correspond individually to the X-ray sources 13 and are directed toward the central axis S. Each through hole 37 is of a shape and a size such that the emitted X rays R never projects beyond the width of the detector 12 in the direction along the central axis S and that X rays R that spread in the circumferential direction without interfering with the X rays R emitted from the X-ray sources 13 in different directions. Thus, the through holes 37 restrict other X rays than the X rays R that are detected by the detector 12. The collimator 36 may be provided corresponding to the X-ray sources 13 in a one-to-one relation or provided collectively in a circular arc for each angular range.

Figure 3:
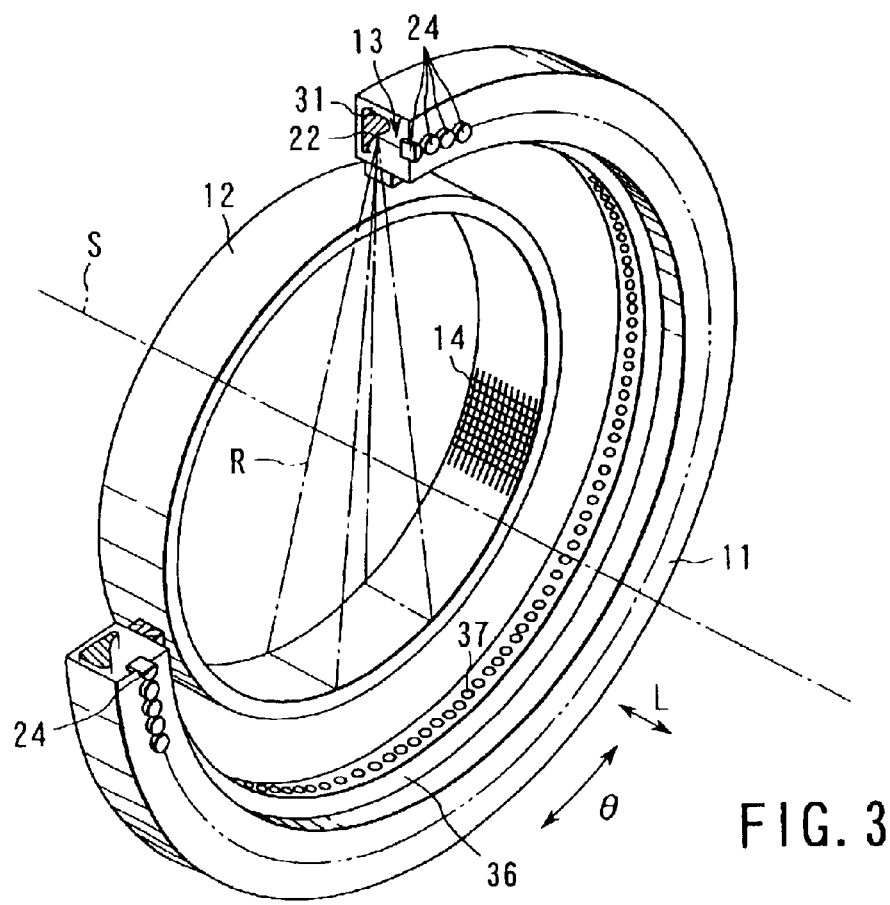
FIG. 3 is a perspective view typically showing the vacuum chamber and the detector of FIG. 1.

The detector 12 detects the X rays R emitted from the X-ray sources 13 in positions symmetrical with respect to the central axis S. As shown in FIG. 3, the detector 12 detects the X rays R on its cylindrical inner peripheral surface. On the inner peripheral surface, detection elements 14 are arranged in a lattice in the circumferential direction ($\theta$-direction) and the direction (L-direction) along the central axis S. In a specific example, 2,048 detection elements 14 are arranged in the $\theta$-direction, and 200 in the L-direction.

Figure 7:
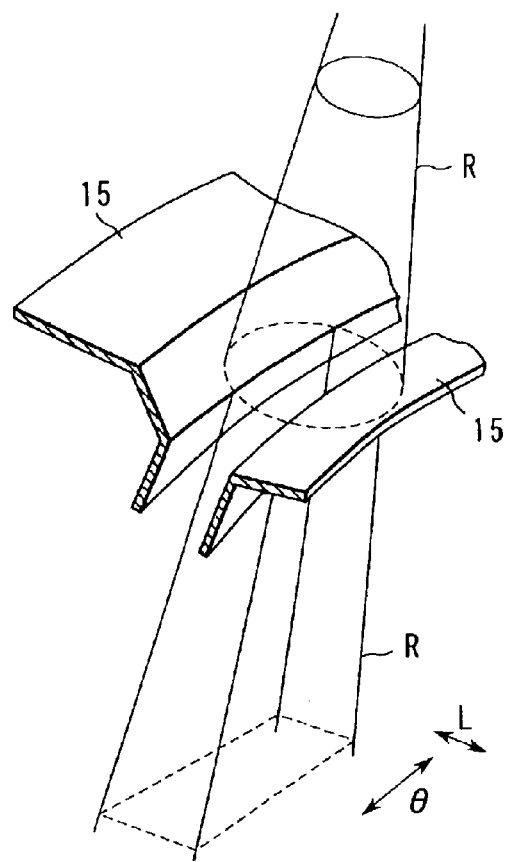
FIG. 7 is a perspective view showing a state in which the shape of X rays is changed by a beam limiter of FIG. 1.

A beam limiter 15 is mounted in a position on the detector 12 near the vacuum chamber 11. The beam limiter 15 is designed to restrict those X rays R from the X-ray sources 13 which project beyond the width of the detector 12. If the X rays R are restricted to prevent from spreading beyond the width of the inner peripheral surface of the detector 12 by the collimator 36 having the round through holes 37, the spread in the $\theta$-direction is also restricted, inevitably. Since the beam limiter 15 can restrict the X rays R in the L-direction, as shown in FIG. 7, the X rays R that never spread beyond the width of the detector 12 can be obtained without restricting the spread in the $\theta$-direction.

The X-ray CT apparatus 10 constructed in this manner delivers a command signal for the acquisition of a tomographic image from a measurement control device (not shown) to an irradiation control element (not shown). The irradiation control element settles the direction of irradiation and the order of irradiation of the X rays R and delivers a control signal to an X-ray generation control device 16 shown in FIG. 1. The X-ray generation control device 16 controls the emission of X rays by controlling the gate 23 of each X-ray source 13 in accordance with the control signal. Patterns for the activation the X-ray sources 13 include a single-slice mode, serial-slice mode, sector-slice mode, single-shot mode, video mode, etc. In the single-slice mode, an optional tomographic image of a patient is picked up with the X-ray sources 13 switched for a revolution around the patient. In the serial-slice mode, a plurality of tomographic images are obtained for a patient who requires a volume inspection while the bed 2 is slid and the X-ray sources 13 are switched. In this case, the volume for the width of the detector 12 can be inspected by only switching the X-ray sources 13 for a revolution around the patient, because the detector 12 of the X-ray CT apparatus 10 has its width in the direction along the central axis S. In the sector-slice mode, a tomographic image of an optional part of the patient P is obtained while the X-ray sources 13 that are located within an optional angular range are switched. In the single-shot mode, the X-ray sources 13 in a desired irradiation position are selected out of the numerous X-ray sources, and X rays are applied. Since the detector 12 has its width in the direction along the central axis S, a X-ray radiographic image corresponding to the width of the detector can be obtained. Thus, the X-ray CT apparatus 10 can be used as if it were a X-ray radiographic apparatus. The X-ray CT apparatus 10 can take the X-ray radiographic image in a desired direction with the patient P lying, that is, without moving the patient P. In the video mode, a continuous stereoimage for the width corresponding to the detector 12 or a continuous image of optional tomographic images can be obtained by electrically switching the X-ray sources 13 at speed.

Figure 5:
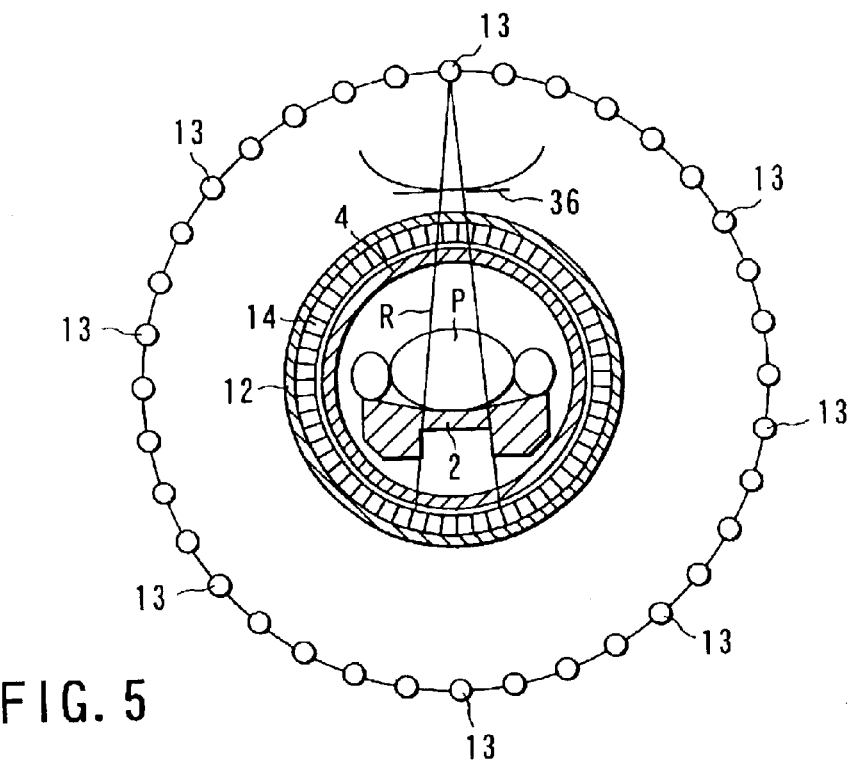
FIG. 5 is a view typically showing the positional relations between X rays emitted from an optional X-ray source of the X-ray CT apparatus of FIG. 1, a collimator for restricting the X rays, an object of inspection, and the detector.
Figure 6:
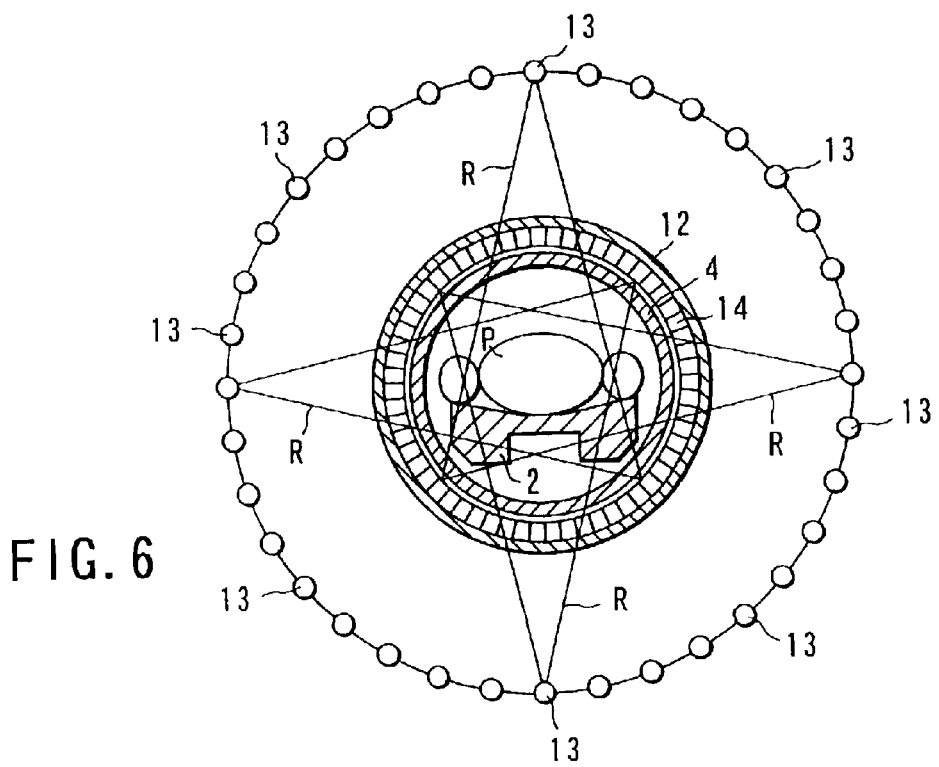
FIG. 6 is a view typically showing a state in which X rays are simultaneously emitted from four X-ray sources of the X-ray CT apparatus of FIG. 1 toward the object of inspection.

Further, single-ray irradiation shown in FIG. 5 or synchronized multi-ray irradiation shown in FIG. 6 can be selected for each mode. When the single-ray irradiation is selected, the dose of X rays applied at a time is small. When the synchronized multi-ray irradiation is selected the load on the patient P is small, because the tomographic image can be obtained in a short time.

An electron beam, which emitted from the cathode 21 as the X-ray generation control device 16 controls the gate 23, runs against the target of the anode 22. The X rays R are radiated in an isotropic manner from the spot of the target that is hit by the electron beam. The radiated X rays R are restricted by the collimator 36 that is attached to the inner peripheral wall of the vacuum chamber 11, and the X rays R having passed through the through holes 37 are emitted toward the patient P. The X rays R emitted from the through holes 37 are further restricted by the beam limiter 15 so as to match the width of the detector 12. After the X rays R are absorbed and attenuated depending on the part of the patient P, they are detected by the detector 12. The detector 12 outputs a signal proportional to the dose of transmitted X rays detected by the detection elements 14 to a preamplifier 17 shown in FIG. 1. The signal output to the preamplifier is sent, as transmitted X-ray information associated with the X-ray sources 13 from which the X rays R are emitted when it is detected, to a data processor (not shown) through a main amplifier (not shown), data recorder (not shown), etc. . . The data processor analyzes each piece of transmitted X-ray information and forms a tomographic image of the patient P, based on the difference in the rate of absorption between the X rays R that depends on the density of each part of the patient P.

The X-ray CT apparatus 10 restricts irradiation regions for the X rays R by the collimator 36 and the beam limiter 15, and never irradiates the patient P with X rays that are not detected by the detector 12, so that the dose of X rays to which the patient P is exposed can be minimized.

The X-ray CT apparatus 10 restricts the spread of the X-ray irradiation regions in the θ-direction of the detector 12 by the collimator 36. Accordingly, the X-ray sources 13 that can simultaneously apply the X rays R without causing the X-ray irradiation regions formed on the detection surface of the detector 12 to interfere with one another can be increased.

Figure 8:
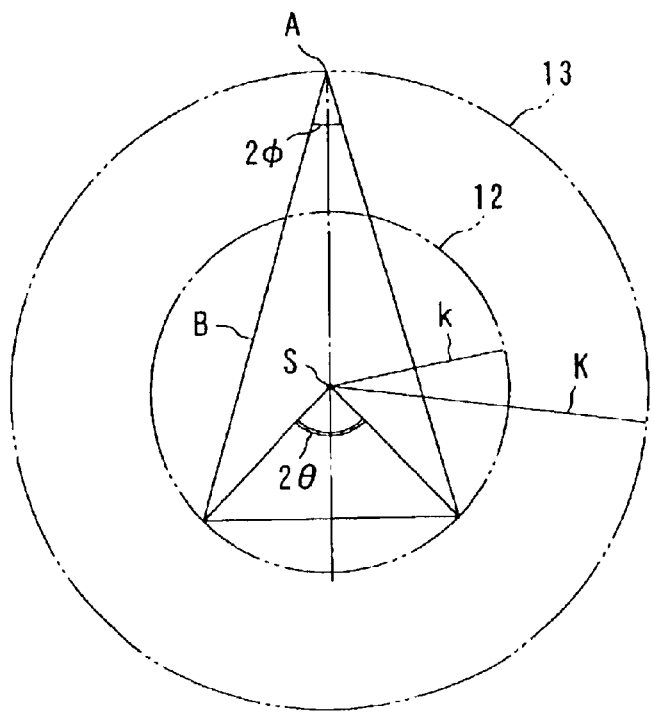
FIG. 8 is a diagram typically showing the positional relation between X-ray sources 13 and the detector 12 of FIG. 1.

In the case where the X rays R are simultaneously applied to the detector 12 from n number of X-ray sources 13 that are arranged at equal distances, an irradiation angle 2φ of the X rays R emitted from each X-ray source 13 through each through hole 37 is settled as follows. Let it now be supposed that the distance from the central axis S to a starting point A at which the X-ray source 13 emits the X rays R is K, the distance from the central axis S to the detection surface of the detector 12 is k, the detection angle of the detector 12 obtained when the irradiation range of the X rays R is viewed from the central axis S is 2θ, and the distance from the starting point A to the end of the irradiation range of the X rays R is B, as shown in FIG. 8. The irradiation angle 2φ of the X rays R emitted from each X-ray source 13 must satisfy:

$$B \cdot \sin \phi \leq k \cdot \sin \theta$$

to prevent the detection angle 2θ being exceeded when the angle to the central axis S is uniform. Since B is written as:

$$B^2 = K^2 + k^2 - 2Kk \cdot \cos(\pi - \theta) = K^2 + k^2 + 2Kk \cdot \cos\theta$$

$$B = \sqrt{K^2 + 30k^2 + 302Kk \cdot \cos\theta}$$

according to the second cosine formula, we get $$\sin\phi \leq \frac{k \cdot \sin\theta}{\sqrt{K^2 + k^2 + 2Kk \cdot \cos\theta}}$$

The detection angle 2θ of the detector that prevents the X rays R emitted from the n number of X-ray sources 13 from interfering with one another is written as:

$$2\theta = \frac{2\pi}{n},$$

and therefore, $$\theta = \frac{\pi}{n}$$

Accordingly, we obtain $$\sin\phi \leq \frac{k \cdot \sin\left(\frac{\pi}{n}\right)}{\sqrt{K^2 + k^2 + 2Kk \cdot \cos\left(\frac{\pi}{n}\right)}}$$

When the angle of the detector 12, which is covered by the irradiation region for the X rays R from one X-ray source 13 on the detection surface of the detector 12, is settled as ninety degrees as shown in FIG. 6, for example, X rays can be synchronously applied from four positions. Thus, when the collimator 36 is arranged so that the X-ray irradiation regions on the detection surface of the detector 12 can cover 360°/n, corresponding to the number n of the X-ray sources 13, the X-ray sources 13 can be switched for one revolution in a time corresponding to 1/n. Therefore, the load on the patient P can be reduced.

Thus, the X-ray CT apparatus 10 obtains a tomographic image by applying the X rays R to the patient P in many directions in a manner such that the numerous X-ray sources 13 that are arranged in a ring around the patient P are switched electrically. Since the X-ray CT apparatus 10 can lessen indistinctness, what is called "blur", of a tomographic image that is attributable to the movement of the patient P, the X-ray CT apparatus 10 can acquire a fine tomographic image in a short time. Since the X-ray CT apparatus 10 restrains the X rays R that are not detected by the detector 12 from being applied to the patient P by the collimator 36 and the beam limiter 15, the dose of X rays to which the patient P is exposed can be minimized. Thus, the X-ray CT apparatus 10 relives the load on the patient P.

The present invention is not limited to the embodiment described above, and various modifications may be effected therein. Although the X-ray CT apparatus described according to the present invention is applied to diagnosis in the medical field in connection with the present embodiment, it may be also applied to the industrial field and the investigation field. Further, the X-ray sources are not limited to the ones described in connection with the present embodiment, X-ray tubes may be adopted for the X-ray sources.

An X-ray CT apparatus according to the present invention is applicable to the fields of medicine, industry, and investigation, and can acquire X-ray radioscopic images, tomographic images, and three-dimensional stereoimages of objects of inspection and their dynamic images.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT apparatus comprising:
a large number of X-ray sources arranged around an object of inspection;
a detector for detecting X rays emitted from the X-ray sources; and
collimators for restricting the X rays, which are emitted from said X-ray sources and which are not applied to a detection surface of said detector, by being located between said X-ray sources and said object of inspection;
wherein said collimators have through holes that are formed as:

$$\sin\phi \leq \frac{k \cdot \sin\left(\frac{\pi}{n}\right)}{\sqrt{K^2 + k^2 + 2Kk \cdot \cos\left(\frac{\pi}{n}\right)}}$$

where K is the distance from the central axis of a concentric circle composed of said large number of X-ray sources to a starting point at which the X-ray sources emit the X rays, k is the distance from said central axis to an inner surface of the detector including a large number of detection elements arranged densely for detecting the X rays in the shape of a concentric circle having said same central axis and capable of detecting the X rays emitted from said X-ray sources, n is the number of X-ray sources to simultaneously apply the X rays, among said large number of X-ray sources, and 2($\phi$) is the angle of the spread of the X ray emitted from said starting point to said detector.

2. The X-ray CT apparatus according to claim 1, wherein said large number of X-ray sources are held in a vacuum chamber in the form of a ring surrounding said object of inspection.

3. The X-ray CT apparatus according to claim 2, wherein said collimators are attached to the outside of an inner peripheral wall of said vacuum chamber.

4. The X-ray CT apparatus according to claim 2, wherein said detector includes a large number of detection elements arranged densely in the shape of a cylinder having the same central axis with a concentric circle composed of said large number of X-ray sources and capable of detecting the X rays.

5. The X-ray CT apparatus according to claim 1, wherein said through holes are provided corresponding individually to said large number of X-ray sources.

6. The X-ray CT apparatus according to claim 5, wherein said through holes restrict the X rays emitted from said X-ray sources with respect to spreads in a direction along the central axis of a concentric circle composed of said large number of X-ray sources and the circumferential direction of said concentric circle.

7. The X-ray CT apparatus according to claim 1, wherein said detector is provided in the shape of a concentric circle having the same central axis with a concentric circle composed of said large number of X-ray sources.

8. The X-ray CT apparatus according to claim 7, wherein said large number of X-ray sources and said detector are relatively shifted in position in the direction along said central axis.

9. The X-ray CT apparatus according to claim 1, which further comprises a beam limiter to restrict the X rays emitted from said X-ray sources within a width, in the direction along a central axis, of said detector shifted in position relatively to said large number of X-ray sources in the direction along said central axis so that the X rays emitted from said X-ray sources are detected by a large number of detection elements arranged densely in the shape of a concentric circle having the same central axis with a concentric circle composed of said large number of X-ray sources.

10. An X-ray CT apparatus comprising:
a main body having a hole in which an object of inspection is located;
a large number of X-ray sources concentrically arranged around said hole;
a vacuum chamber in the form of a ring surrounding said hole and holding said X-ray sources;
a collimator mounted along the an inner peripheral wall of said vacuum chamber and having through holes corresponding to said X-ray sources;
a detector including a large number of detection elements arranged densely in the shape of a cylinder having the same central axis with a concentric circle composed of said large number of X-ray sources, with the detection surface thereof facing toward said central axis, and capable of detecting the X rays emitted from said X-ray sources;
a bed having a slide mechanism and a lift device, and capable of positioning said object of inspection in said hole; and
a beam limiter located between said large number of X-ray sources and said object of inspection, and capable of restricting the spread of said X rays in the direction along said central axis within the width of said detector in the direction along said central axis;
wherein said collimators have through holes that are formed as:

$$\sin\phi \leq \frac{k \cdot \sin\left(\frac{\pi}{n}\right)}{\sqrt{K^2 + k^2 + 2Kk \cdot \cos\left(\frac{\pi}{n}\right)}} \qquad 5$$

where K is the distance from the central axis of a concentric circle composed of said large number of X-ray sources to a starting point at which the X-ray sources emit the X rays, k is the distance from said central axis to an inner surface of the detector including a large number of detection elements arranged densely for detecting the X rays in the shape of a concentric circle having said same central axis and capable of detecting the X rays emitted from said X-ray sources, n is the number of X-ray sources to simultaneously apply the X rays, among said large number of X-ray sources, and 2($\phi$) is the angle of the spread of the X rays emitted from said starting point to said detector.

* * * * *